United States Patent
Campion et al.

[11] Patent Number: 6,151,119
[45] Date of Patent: Nov. 21, 2000

[54] APPARATUS AND METHOD FOR DETERMINING DEPTH PROFILE CHARACTERISTICS OF A DOPANT MATERIAL IN A SEMICONDUCTOR DEVICE

[75] Inventors: Alan Campion; Charles E. May; Tim Z. Hossain, all of Austin, Tex.

[73] Assignee: Advanced Micro Devices, Sunnyvale, Calif.

[21] Appl. No.: 08/995,022

[22] Filed: Dec. 19, 1997

[51] Int. Cl.$^7$ .......................... G01B 11/06; G01N 21/00
[52] U.S. Cl. ............................. 356/381; 356/432
[58] Field of Search ................. 356/432, 432 T, 356/381

[56] References Cited

U.S. PATENT DOCUMENTS

| | | | |
|---|---|---|---|
| 4,188,123 | 2/1980 | Kleinknecht | 356/354 |
| 4,743,569 | 5/1988 | Plumton et al. | 437/247 |
| 4,807,994 | 2/1989 | Felch et al. | 356/326 |
| 5,105,362 | 4/1992 | Kotani . | |
| 5,180,690 | 1/1993 | Czubatyj et al. | 437/233 |
| 5,229,304 | 7/1993 | Chang et al. | 437/7 |
| 5,270,536 | 12/1993 | Malhotra . | |

FOREIGN PATENT DOCUMENTS

| | | |
|---|---|---|
| 0 631 304 A2 | 12/1994 | European Pat. Off. . |
| 0 631 304 A3 | 12/1994 | European Pat. Off. . |
| 0 735 378 A2 | 10/1996 | European Pat. Off. . |
| 0 735 378 A3 | 10/1996 | European Pat. Off. . |
| 0 827 192 A2 | 3/1998 | European Pat. Off. . |

OTHER PUBLICATIONS

Ochiai, M. et al., "Analysis of SiO$_2$/InP Interfaces Using Gated Photoluminescence and Baman Spectroscopy", Fourth International Conference on Indium Phosphide and Related Materials, Apr. 21–24, 1992 Newport, Rhode Island, pp. 658–660.

de Wilton et al., "A Raman study of the dopant distribution in submicron pn junctions in B$^+$or BF$_2^+$ ion implanted silicon", in "Advanced Processing and Characterization of Semiconductors III", *Proceedings of SPIE—The International Society of Optical Engineers*, vol. 623, pp. 26–34 (Jan. 22–24 1986).

de Wilton et al., "Nondestructive ion–implant monitoring user laser Raman spectroscopy", *Canadian Journal of Physics*, 65(8):821–830 (Aug. 1987).

Huang et al., "Depth profiling of hydrogen passivation of boron in Si(100)", *Physical Review B*, 46(7):4086–4091 (Aug. 15, 1992).

Nakano et al., "Raman scattering in polycrystalline silicon doped with boron", *Journal of Applied Physics*, 72(8):3641–3647 (Oct. 15, 1992).

*Primary Examiner*—Frank G. Font
*Assistant Examiner*—Zandra V. Smith
*Attorney, Agent, or Firm*—Crawford PLLC

[57] ABSTRACT

An apparatus and method for the determination of a depth profile and/or one or more depth profile characteristics of a dopant material in a semiconductor device includes a light source which can illuminate the device at two or more illumination wavelengths, a detector that receives scattered light from the semiconductor device and determines an intensity characteristic for one or more Raman spectral lines attributable to the presence of the dopant material in the semiconductor device. The intensity characteristics of the Raman spectral lines can then be used to determine the depth profile or depth profile characteristics using profile constants measured from known samples at each of the illumination wavelengths. This apparatus and method can be used in-line because it is noninvasive, relatively quick, and nondestructive.

22 Claims, 5 Drawing Sheets

APPARATUS AND METHOD FOR DETERMINING DEPTH PROFILE CHARACTERISTICS OF A DOPANT MATERIAL IN A SEMICONDUCTOR DEVICE

FIELD OF THE INVENTION

The present invention is directed generally to semiconductor devices and, more particularly, to a method and apparatus for determining a depth profile or one or more depth profile characteristics of a dopant material in a region of a semiconductor device.

BACKGROUND OF THE INVENTION

Current semiconductor technology typically involves incorporating dopant material in various portions of a semiconductor device including, for example, the substrate of the device or a layer formed over the substrate. One typical example of a semiconductor device is a metal-oxide-semiconductor (MOS) transistor. The principal elements of a typical MOS semiconductor device are illustrated in FIG. 1. The device generally includes a semiconductor substrate 101 on which a gate electrode 103 is disposed. The gate electrode 103 acts as a conductor and is typically formed of polysilicon with a dopant material at a desired concentration.

Source/drain regions 105 are formed in the semiconductor substrate 101 adjacent to the gate electrode 103. Generally, the source/drain regions 1 05 are formed by implanting a dopant material into the substrate. Following the dopant implant, the substrate is typically annealed to drive the dopant material deeper into the substrate 101 and to more uniformly dope the source/drain regions 105. The thickness of each source/drain region 105 is generally a function of the dopant concentration and the amount of annealing.

A channel region 107 is formed in the semiconductor substrate 101 beneath the gate electrode 103 and separates the source/drain regions 105. The channel is typically lightly doped with a dopant material of a type opposite that of the source/drain regions 105. The gate electrode 103 is generally separated from the semiconductor substrate 101 by an insulating layer 109, for example an oxide layer such as $SiO_2$.

One commonly used substrate material is silicon. Dopant materials for use with silicon are often electron donors or acceptors (or, alternatively, hole acceptors and donors), such as Group III and Group V elements including, for example, boron, nitrogen, arsenic, and phosphorus. The operational parameters of a particular semiconductor device often depend, at least in part, on the concentration and depth profile of the dopant material. In some cases, the allowed tolerances in the variation in dopant concentration may be very narrow. Therefore, it is desirable to have methods to determine the dopant concentration and profile in a semiconductor device.

Determination of the concentration and profile of a dopant material in a region of a semiconductor device, such as the gate electrode, source/drain regions, or channel region can be done in several ways. One method includes measuring particular electrical properties of a region of the semiconductor device which may be characteristic of the presence of the dopant material or characteristic of damage caused by the incorporation of the dopant material in the semiconductor by methods such as ion implantation. Many of these electrical property measurement techniques, however, are limited to the determination of the concentration of the dopant material. Those which are used to determine the profile of the dopant in the semiconductor are typically destructive and invasive. For example, depth profile measurement techniques may include measuring the electrical properties of a doped region, removing a portion of the doped region, and remeasuring the electrical properties of the region. The measurements are typically obtained at intervals as increasing amounts of the doped region are removed to provide a depth profile of the region.

Another conventional method for determining the concentration and, more particularly, the depth profile of the dopant material is secondary ion mass spectroscopy (SIMS). This method involves bombarding the surface of a semiconductor region with an ion beam which causes the ejection of material from the semiconductor surface. The mass of the ejected material is measured by a mass spectrometer to determine the composition of the semiconductor device. A profile of dopant concentration can be obtained by observing the ejected material over time. This method is also invasive and destructive.

One noninvasive method is Nuclear Depth Profiling (NDP) which requires that the semiconductor device be bombarded by energetic neutrons from a source, such as a nuclear reactor. The neutrons bombard the semiconductor device and cause the ejection of measurable particles as the neutrons encounter a dopant material like boron. This method, however, cannot be used on the fabrication line because it requires a source of energetic neutrons.

SUMMARY OF THE INVENTION

Generally, the present invention relates to a method and apparatus for determining the concentration and depth profile of a dopant in a semiconductor region noninvasively and nondestructively. Such a method and apparatus can be incorporated in the fabrication line to determine the concentration, depth profile, and/or one or more depth profile characteristics of dopant material in a region of a semiconductor device quickly and nondestructively. This information may be used to adjust the parameters of the fabrication process to correct for any deviations from the device specifications.

One embodiment of the invention is a method for determining at least one depth profile characteristic of a dopant material in a region of a semiconductor device. The method includes illuminating the region with light at each of one or more illumination wavelengths to produce scattered light. For each of the one or more illumination wavelengths, an intensity characteristic of the scattered light is determined for one or more spectral lines which are attributable to the presence of the dopant material in the region. At least one depth profile characteristic of the dopant material is determined using the intensity characteristics and the illumination wavelengths.

Another embodiment of the invention is a method for determining a depth profile of a dopant material in a region of a semiconductor device. The method includes illuminating the region with light at two or more illumination wavelengths and obtaining for each of the two or more illumination wavelength at least a portion of an associated Raman spectrum. For each Raman spectrum, an intensity characteristic of one or more spectral lines attributable to the presence of the dopant material in the region is determined. Using the intensity characteristics for each Raman spectrum and the respective illumination wavelengths, the depth profile of the dopant material in the region is determined.

A further embodiment is a method for in-line determination of at least one depth profile characteristic of a plurality of semiconductor devices which includes doping a target region of one or more semiconductor devices with a dopant material using a set of dopant parameters. At least one test semiconductor device is chosen from among the one or more semiconductor devices. The target region of the test semiconductor device is illuminated with light at at least one illumination wavelength to produce scattered light. For each of the at least one illumination wavelengths, an intensity characteristic of the scattered light is determined for one or more spectral lines attributable to the presence of the dopant material in the semiconductor device. The at least one depth profile characteristic of the dopant material is then determined using the intensity characteristics and the illumination wavelengths.

Yet another embodiment of the invention is an apparatus for the production of semiconductor devices. The apparatus includes a doping apparatus for doping a region of the semiconductor devices with a dopant material based on a set of doping parameters and an in-line apparatus which determines at least one depth profile characteristic of the dopant material in the target region of one or more of the doped semiconductor devices.

Another embodiment is an apparatus for determining the depth profile of a dopant material in a semiconductor device. The apparatus includes a light source capable of producing light at two or more illumination wavelengths. The apparatus also has a detector to measure an intensity of light scattered from a semiconductor device which is illuminated by the light source. The detector measures the intensity of scattered light for one or more spectral lines at each illumination wavelength. In addition, the apparatus includes a processor to determine the depth profile from the measured intensities.

The above summary of the present invention is not intended to describe each illustrated embodiment or every implementation of the present invention. The Figures and the detailed description which follow more particularly exemplify these embodiments.

BRIEF DESCRIPTION OF THE DRAWINGS

The invention may be more completely understood in consideration of the following detailed description of various embodiments of the invention in connection with the accompanying drawings, in which.

Figure 1:
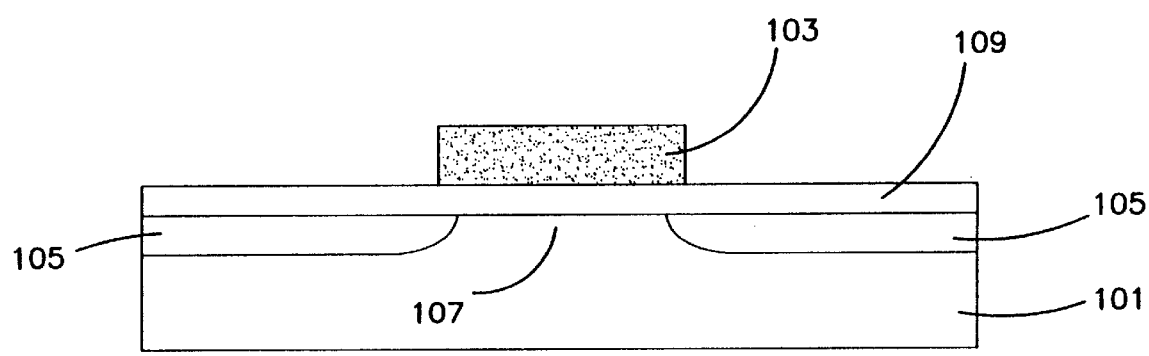
FIG. 1 is a cross-sectional view of a conventional MOS transistor.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION OF THE VARIOUS EMBODIMENTS

The present invention is believed to be applicable to a number of different types of semiconductor devices (such as MOS, CMOS, and BiCMOS transistors) which have doped regions. While the present invention is not so limited, an appreciation of various aspects of the invention will be gained through a discussion of the examples provided below.

The present invention is directed to the determination of the concentration, depth profile, and/or one or more depth profile characteristics of a dopant material in a target region of a substrate using Raman spectroscopy. The target region may, for example, be any layer of a semiconductor device which has been doped, including the substrate, polysilicon gate layers, dielectric layers, etc. The term "depth profile" will be used herein to describe the concentration of a dopant material as a function of distance from a reference point on the semiconductor device (typically the top surface of a layer or the substrate). The term "depth profile characteristics" will be used to indicate characteristics that describe the distribution of dopant in the material, including, for example, the position of a peak dopant concentration and/or a width characteristic (e.g., standard deviation) of the distribution.

Figure 2:
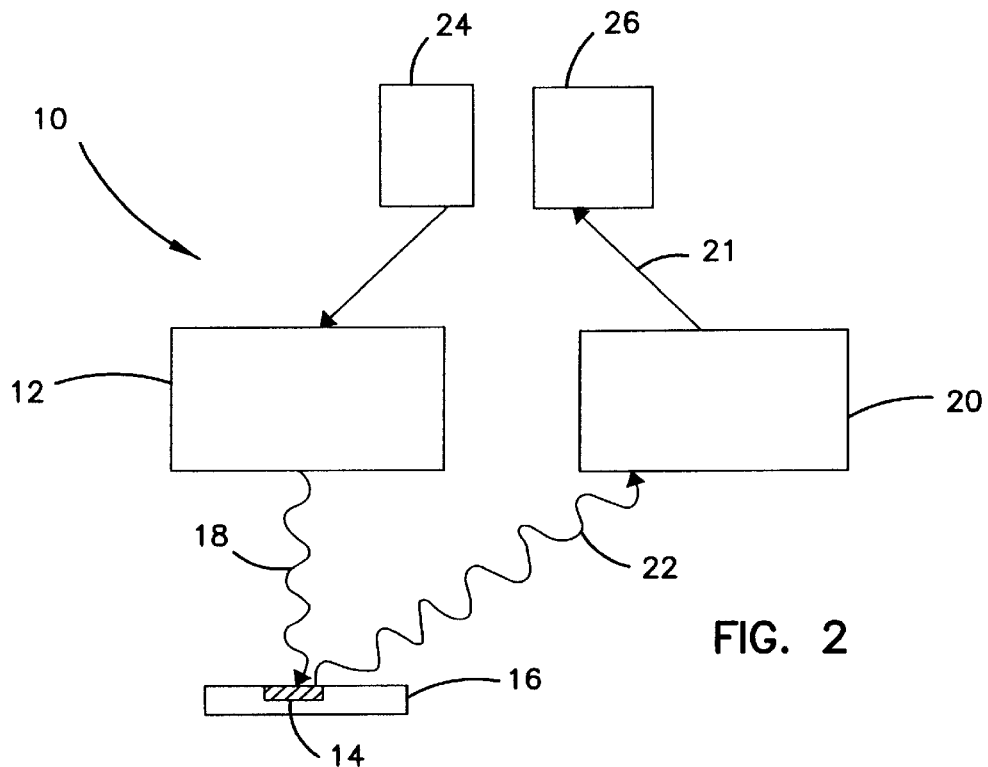
FIG. 2 is a diagrammatic illustration of an exemplary depth profiling apparatus in accordance with one embodiment of the invention.

FIG. 2 illustrates a depth profiling apparatus 10 in accordance with an embodiment of the invention. The depth profiling apparatus 10 generally uses Raman spectroscopy to obtain a depth profile, one or more depth profile characteristics, and/or a concentration of a dopant material in a target region 14 of a semiconductor device 16. The semiconductor device is typically a device in the process of being fabricated although the invention is not so limited.

The depth profiling apparatus 10 includes a light source 12 which illuminates the target region 14 of the semiconductor device 16 with illumination light 18. A detector 20 receives scattered light 22 from the semiconductor device 16 and generates a signal in response to the scattered light. A light source control system 24 is typically provided to control the wavelength and/or operation of the light source 12. A detection system 26 is typically provided to receive the signal 21 from the detector 20 and optionally control the detector 20 by, for example, limiting the range of light wavelengths that are received by the detector 20.

The light source 12 is typically capable of providing light at two or more illumination wavelengths. The light source 12 may contain one or more subunits that each provide monochromatic light (e.g., light having a single wavelength or a narrow band of wavelengths). In one embodiment, the light source 12 includes a single laser which emits monochromatic light and may be tuned to one or more frequencies, thereby enabling the laser to provide light at two or more wavelengths. In another embodiment, the light source 12 includes two or more lasers, each of which provide light at different illumination wavelengths. It will be appreciated that the invention is not limited to the exemplary light sources discussed above. Other light sources and methods for obtaining Raman spectra from those light sources may also be used.

The detector 20 is used to receive light 22 scattered from the target region 14 of the semiconductor device 16. Examples of suitable detectors include photomultipliers, photodiodes, or CCD (charge coupled device) arrays. Examples of suitable detectors include FT Raman detectors, spectrographs with multichannel detectors, and detectors that include narrow bandpass light filters for use with laser light sources.

As another example, the detector 20 may include a monochromator to control the wavelength of light that is received at the detector at any given time. The monochromator typically includes a diffraction grating or prism which spreads out the light according to wavelength. The light is then directed towards a wall having a narrow slit. Only light having a particular wavelength will pass through the slit. The wavelength of light that passes through the slit can be changed by moving the slit or by altering the position of the grating or prism. This movement can be done either manually or mechanically. In many cases, the movement is controlled by a computer. In this manner, the monochromator may scan a particular range of wavelengths to obtain the Raman spectrum. In other embodiments of the invention, the monochromator may only allow certain wavelengths of light to be detected, particularly when only a small portion of the Raman spectrum is needed for determination of the depth profile, one or more depth profile characteristics, and/or concentration of the dopant material. The monochromator may be controlled by a device, such as a computer, which directs the monochromator to allow only the wavelengths of interest through the narrow slit. Other detectors and methods of detection of scattered light are known and may be used to obtain spectral information.

Figure 3:
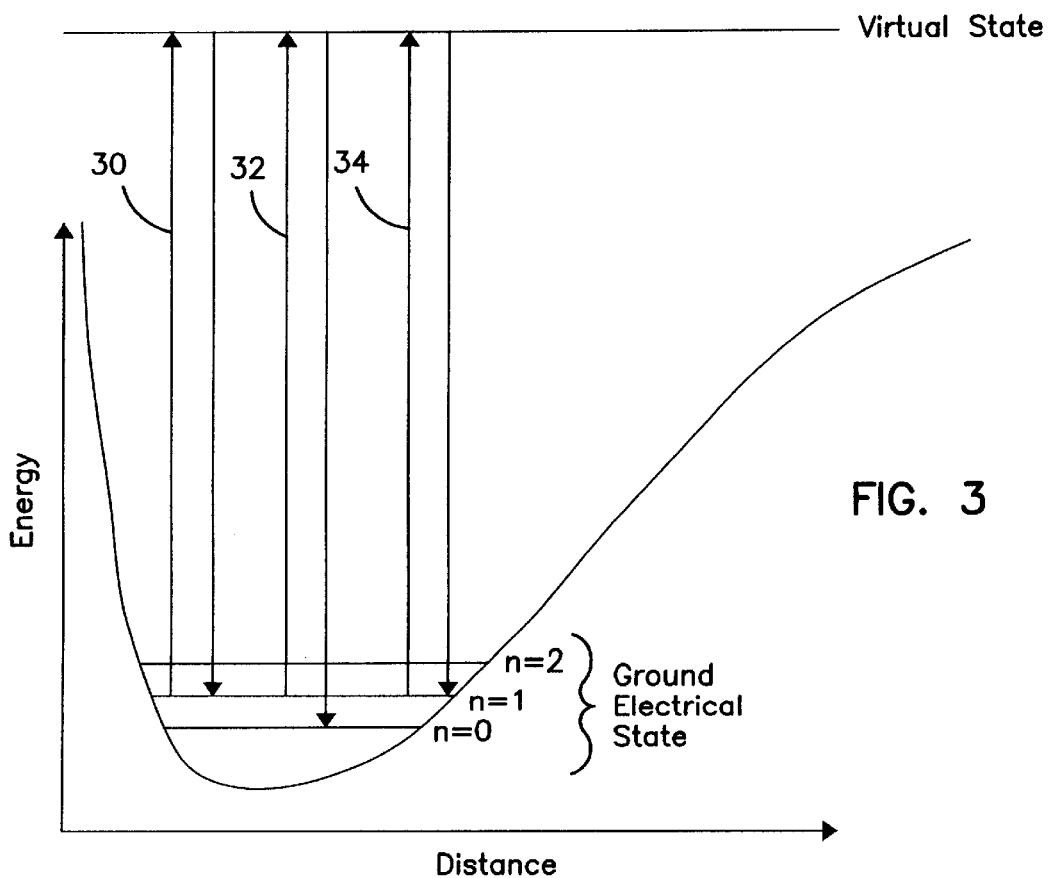
FIG. 3 is an energy level diagram illustrating Rayleigh and Raman scattering mechanisms.
Figure 4:
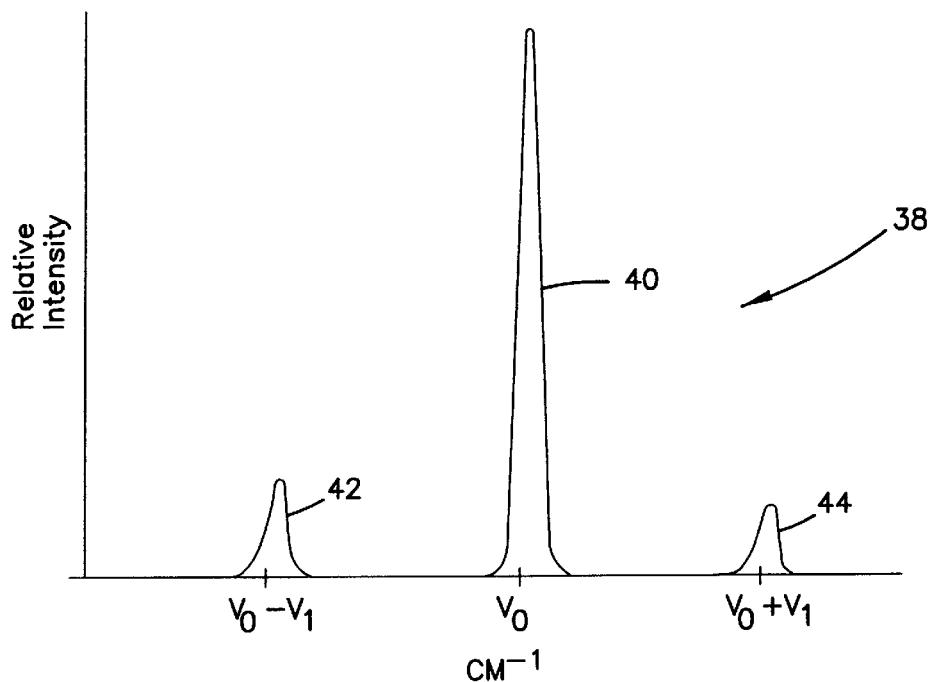
FIG. 4 is a diagram illustrating the expected Rayleigh and Raman scattering lines.

The Raman spectrum of the scattered light 22 varies with the characteristics of the target region 14 being illuminated. To illustrate the phenomenon of Raman scattering, reference will be made to an exemplary energy level diagram (FIG. 3) and an exemplary Raman spectrum (FIG. 4). Both FIGS. 3 and 4 are provided by way of example, and are not intended to be illustrative of the illumination of a particular target region.

A Raman spectrum is typically obtained by illuminating a sample (such as the target region 14 of the semiconductor device 16) with light and then detecting the light which is scattered (i.e., absorbed and then reemitted) from the sample. Most of the scattered light is due to Rayleigh scattering which results in the emission of light having the same wavelength as the illumination light. Rayleigh scattering can be thought of as the elastic scattering of light by a sample and can be described (although no particular theory is necessary to the invention) as the absorption of illuminating light and subsequent emission of scattered light having the same wavelength, shown as path 30 in FIG. 3.

Raman scattering, on the other hand, is an inelastic scattering process. This scattering process can be thought of as the absorption of the illuminating light to induce an electron into an excited state (sometimes called a "virtual state") followed by emission of scattered light as the electron returns to the same ground electronic state, but a different vibrational energy state, as depicted by paths 32 and 34 of FIG. 3. Light scattered in this manner (hereinafter "Raman scattered light") differs in energy from the illumination light by an amount corresponding to the energy difference between the initial vibrational state (e.g., n=1) and the final vibrational state (e.g., n=0 or 2). The wavelength $\lambda$ of the Raman scattered light varies inversely with the energy E of the light in accordance with the following relationship:

$$E = hc/\lambda \qquad (1)$$

where h is Planck's constant and c is the speed of light. Hence, the wavelength of the Raman scattered light will differ from the wavelength of the illuminating light.

By measuring the intensity of the scattered light over a range of wavelengths, a Raman spectrum can be obtained. An exemplary Raman spectrum 38 is illustrated in FIG. 4. More typically only one half of the spectrum is used as the spectral features are symmetrically spaced about the illumination wavelength. Furthermore, features on the long wavelength side of the spectrum are typically more intense than those on the short wavelength side. In this exemplary Raman spectrum, $v_0$ is the frequency of the illuminating light and $v_1$ is the frequency of light which would excite an electron from one vibrational state to another (e.g., from the n=0 to the n=1 vibrational state in FIG. 3). This frequency $v_1$ is related to the energy difference between the two vibrational states by the following equation:

$$E = hv \qquad (2)$$

where E is the difference in energy between the two states and h is Plank's constant.

Typically, a large spectral line 40 is found at $v_0$. This spectral line results from Rayleigh scattering. Much smaller spectral lines 42, 44 are found at $v_0-v_1$ (Stokes line) and $v_0+v_1$ (Anti-Stokes line). These are Raman spectral lines. In most Raman spectra there are many spectral lines corresponding to different vibrational modes (e.g., molecular or lattice vibrations) in the sample. Raman spectral lines are often identified by the difference in frequency (typically measured in wavenumbers, $cm^{-1}$) between the spectral line (e.g., $v_0-v_1$) and the illumination light ($v_0$).

The usefulness of the Raman spectrum arises from the dependence of the vibrational frequencies (i.e., the spectral lines) on the atomic structure of the object being illuminated. Thus, by observing the Raman spectral lines associated with a particular portion of the atomic structure, information regarding the environment around that structure, and in particular, information regarding changes in that environment can be monitored.

With respect to the study of dopant material in semiconductor devices, Raman spectral features attributable to the presence of the dopant material in the semiconductor material can be observed. For example, a Raman line near 620 $cm^{-1}$, corresponding to a phonon frequency of the material, is associated with boron doping in a silicon substrate. Typically, as the dopant concentration becomes greater, the intensity of the 620 $cm^{-1}$, Raman line increases.

Figure 6:
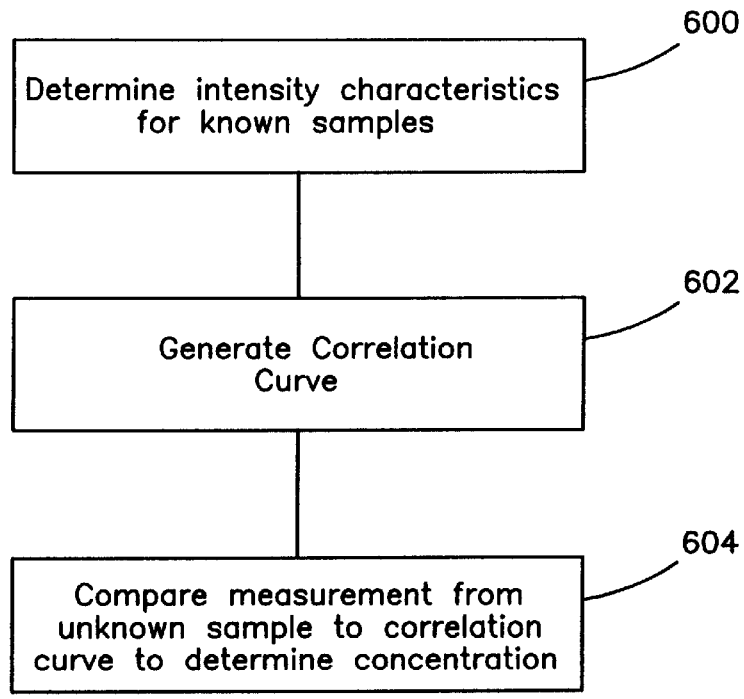
FIG. 6 is a flowchart illustrating an exemplary process for determining the concentration of a dopant material according to an embodiment of the invention.

FIG. 6 illustrates one exemplary process for determining the concentration of a dopant material in a target region of a semiconductor device. This process includes measuring one or more intensity characteristics of the scattered light. Each intensity characteristic is associated with a Raman line (i.e., wavelength range) which is attributable to the presence of the dopant material. Consistent with the exemplary process of FIG. 6, a series of samples having a known amount of dopant material or a known average concentration of dopant material is obtained. For each known sample, an intensity characteristic of a particular Raman line or lines attributable to the presence of the dopant material in the semiconductor device is measured, as indicated at block 600. The intensity characteristic is indicative of the amount of dopant material or the average concentration of dopant material. Exemplary methods for measuring an intensity characteristics of a Raman line are provided below.

Using the measured intensity characteristic(s), a correlation curve is generated, as indicated at block 602. This may be done using a variety of well-known techniques, including, for example, methods such as linear or non-linear least squares analysis or other curve-fitting techniques.

The concentration of a dopant material in an unknown sample can then be determined using the correlation curve and measured intensities of the Raman line or lines for the unknown sample, as indicated in block 604. Typically, the measurements of an intensity characteristic of a Raman spectral line from an unknown sample are performed using illumination light having the same wavelength as the illumination light used to illuminate the known samples. In addition, the physical characteristics (e.g., type of substrate or layer and type of dopant material) of the samples used to generate the correlation curve are typically similar to the physical characteristics of the unknown sample. The intensity of light scattered by a sample is dependent on both the material from which the light is scattered and the wavelength of the illuminating light.

The wavelength dependence of the scattering light intensity is due, at least in part, to the wavelength dependence of the index of refraction and the absorption coefficient of the material. Another source of the wavelength dependence of the intensity of the light from the light source is the difference in emission intensities of the light source at various wavelengths. Furthermore, the detector will also typically be more responsive to some wavelengths than to others.

This wavelength dependence of the measurements may make comparisons between measurements of the same spectral line for different illumination wavelengths difficult. However, it may be possible to obtain a normalized intensity for the dopant-dependent spectral lines using another spectral line which is relatively independent of the presence of the dopant. For example, a silicon phonon spectral line is found at about 530 cm$^{-1}$. The intensity of this particular spectral line is substantially independent of the boron concentration in the silicon substrate so that spectra obtained at different wavelengths may be normalized using the ratio of intensities of the 530 cm$^{-1}$ spectral line at the two different wavelengths. This normalization process may overcome many of the instrumental wavelength dependencies in signal intensity, such as the light source intensity and the wavelength dependence of the detector.

Figure 7:
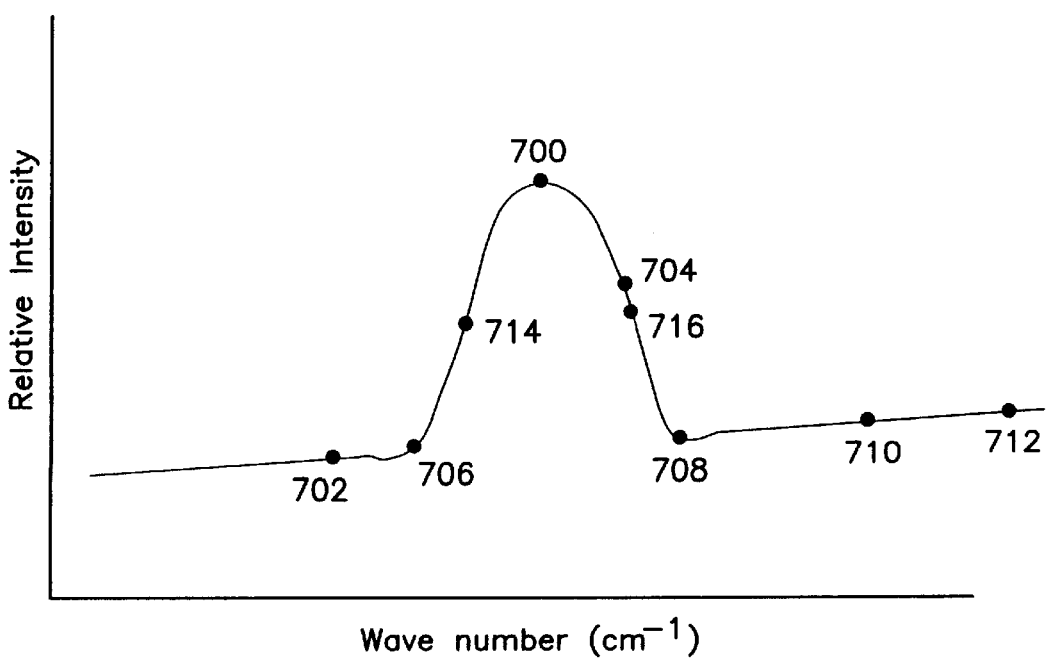
FIG. 7 is an exemplary Raman spectral line.

As noted above, a number of different intensity characteristics of a Raman spectral line can be used with the invention. Exemplary intensity characteristics will be described with reference to a Raman spectral line illustrated in FIG. 7. One example of a suitable intensity characteristic is the height 700 of the Raman spectral line. Another suitable intensity characteristic is the relative intensity of scattered light at any frequency (e.g., 704) in the Raman spectral line. Optionally, the intensity of light at a second frequency or frequency range (e.g., between 710 and 712) may be measured in a portion of the Raman spectrum that is relatively devoid of spectral features to obtain a baseline measurement.

A further example of a suitable intensity characteristic is the area under the Raman spectral line which can be calculated by integrating the intensity of the line between two points. The points can be chosen in a number of different ways, so long as there is consistency between the measurements. For example, the points may correspond to points at the bottom of the Raman spectral line (e.g., 706 and 708). In some embodiments, these points can be chosen by determining a baseline for the Raman spectrum using, for example, regions of the Raman spectrum where there are no Raman spectral lines (e.g., between 710 and 712). The set of points can then be chosen, for example, as the points at which the Raman spectral line intercepts the baseline. Other sets of points can be chosen, for example, points at half height of the Raman spectral line (e.g., 714 and 716). The intensity can then be integrated between these points to give an area under the line which can be used, for example, to form a correlation curve, if the dopant concentration is known, or for determining the concentration of the dopant using a previously measured correlation curve.

The intensity of the light scattered when an illuminating lightbeam is directed at the surface of the sample is also a function of the depth z that the light penetrates into the region. In accordance with one embodiment of the invention, the dependence of intensity on penetration depth is used to determine the depth profile or one or more depth profile characteristics of the dopant material in the semiconductor device.

The intensity of scattered light may be described by the following relationship:

$$I = A(\lambda, \lambda')B(\lambda)B(\lambda')\int_0^T e^{\frac{-4\pi k(\lambda)z}{\lambda}} C(z) e^{\frac{-4\pi k(\lambda')z}{\lambda'}} dz \qquad (3)$$

in which $\lambda$ is the wavelength of the illumination light, $\lambda'$ is the wavelength of the Raman scattered light, and T is the thickness of the sample or a region of interest in the sample. $A(\lambda,\lambda')$ is a factor which depends on the configuration of the Raman spectrometer including such elements as the relative intensity of light provided by the light source and the relative detection capability of the detector. $B(\lambda)e^{-4\pi k(\lambda)z/\lambda}$ describes the absorption of light by the sample where $k(\lambda)$ is the absorption coefficient and $B(\lambda)$ is a scaling factor. $B(\lambda')$ $e^{-4\pi k(\lambda')z/\lambda'}$ describes the absorption of the Raman scattered light as it is exiting the sample where $k(\lambda')$ is the absorption coefficient and $B(\lambda')$ is a scaling factor.

$C(z)$ is the depth profile of the dopant in the sample. Typically, this depth profile will be modeled by a mathematical expression. For example, the depth profile can be modeled as a Gaussian distribution, $C(z)=Ce^{-a(z-z_0)^2}$, where C, a, and $z_0$ are parameters of the distribution. In the Gaussian distribution, C corresponds to the concentration of the dopant within the general region probed by the illumination light, a is a characteristic width (e.g., standard deviation) of the dopant distribution, and $z_0$ is the position of the peak concentration of the dopant. Determining these parameters gives the depth profile.

In some embodiments, it may be sufficient to determine one or more characteristics of the depth profile, instead of the complete profile. Such characteristics include, for example, the position of the peak concentration, e.g., $x_0$ in the Gaussian distribution, or a characteristic width (e.g., a standard deviation) of the concentration distribution, e.g., a in the Gaussian distribution.

Other distributions may also be used to model the depth profile of the dopant material. These models may included one or more parameters, some of which may be characteristics of the distribution. Models that include more parameters than the Gaussian distribution may be used in cases, such as multiple implants of doping material or to generate a more accurate model of the depth profile.

Because $\lambda$ and $\lambda'$ are relatively close in frequency (and therefore $B(\lambda) \approx B(\lambda')$ and $k(\lambda) \approx k(\lambda')$), equation (3) can be approximated as:

$$I \approx A(\lambda)B^2(\lambda)\int_0^T \left(e^{\frac{-4\pi k(\lambda)z}{\lambda}}\right)^2 C(z)dz \qquad (4)$$

This relationship may be used to simplify the processing of the data. Relationships similar to equations (3) and (4) can be determined for other intensity characteristics.

The intensity of the scattered light, according to equations (3) and (4), is the integral of a product of functions which depend on depth and wavelength. Values for the wavelength dependent functions (e.g., $A(\lambda)$, $B(\lambda)$, $B(\lambda')$, $k(\lambda)$, and $k(\lambda')$) may be obtained for each illumination wavelength, as will be discussed below. These wavelength dependent values will be referred to as "profile constants". These profile constants are often determined for each illumination wavelength and type of material, as described below.

The depth profile parameters may be determined from the measured intensity characteristics using standard calculational techniques and the previously determined profile constants. Such calculational techniques include well-known numerical techniques which may be performed by, for example, a processor that receives the intensity characteristic data. These numerical techniques include, for example, linear or nonlinear least squares estimation and numerical integration methods. One or more dopant profile parameters may be estimated by other techniques and incorporated in the calculation of the depth profile or other parameters to reduce the complexity of the calculations and/or the amount of data needed to determine the desired quantities. For example, the dopant concentration or peak position may be estimated based on dopant implant parameters.

Figure 8:
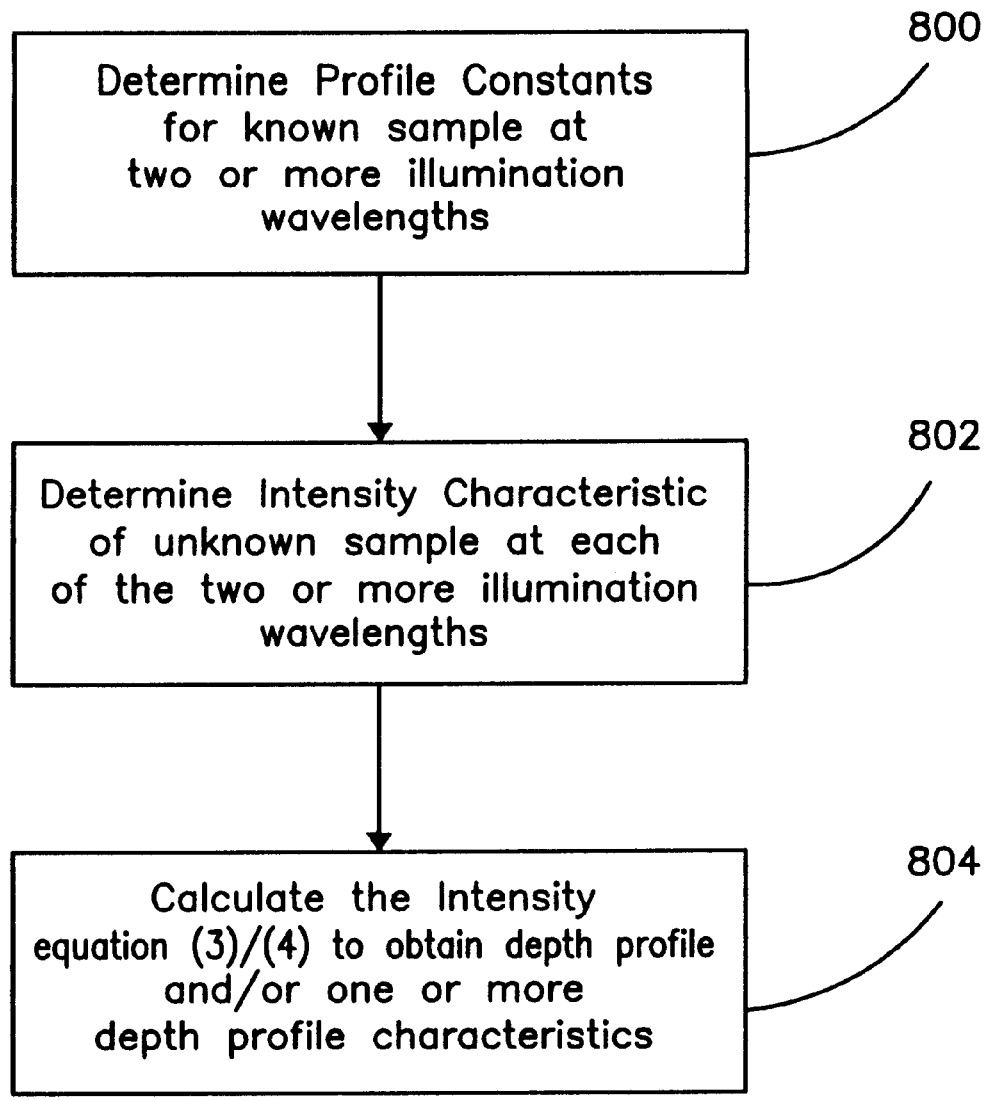
FIG. 8 is a flowchart illustrating an exemplary process for determining the depth profile of a dopant material according to another embodiment of the invention.

FIG. 8 illustrates an exemplary process for determining the depth profile of a dopant material in a target region of a semiconductor device. First, the profile constants are determined for two or more illumination wavelengths as indicated in block 800. The number of illumination wavelengths is typically selected in consideration of the range of values of the optical constant, $k(\lambda)$, as will be discussed below.

The profile constants may be determined, for example, by illuminating one or more known samples of the dopant material at the two or more illumination wavelengths, measuring the intensity characteristics of one or more Raman lines attributable to the dopant materials at each wavelength, and generating a correlation curve. This may be done in a similar manner to that discussed above with respect to FIG. 6. The profile constants $A(\lambda,\lambda')$, $B(\lambda)$ and $B(\lambda')$ may, for example, be determined from fitting parameters for the correlation curve.

The optical constants $k(\lambda)$ and $k(\lambda')$ may be determined by standard spectroscopic ellipsometry measurements. Ellipsometry is a well-known technique for the measurement of both the index of refraction, n, and the absorption coefficient, k, of materials.

Typically, the measurements of the wavelength dependent terms of equations (3) and (4) are performed for each different material that will be used. The absorption coefficient, $k(\lambda)$, is material dependent. However, for some materials which have similar chemical structures, these terms may be relatively equal.

The number of different illumination wavelengths that are needed for determining a depth profile may depend in part on the range of values of the absorption coefficients, $k(\lambda)$, as well as the number of parameters that are used in the model of the dopant distribution. Typically, $1/k(\lambda)$ can be considered as the depth at which 63% of the light has been absorbed. About 86.5% of the light has been absorbed at a depth of about $2/k(\lambda)$. Thus, the term, $k(\lambda)$ can be used as a guide for the depth at which the light of a particular wavelength can penetrate into the sample. Relatively large values of $k(\lambda)$ indicate light that can not penetrate far into the sample and, therefore, the Raman spectral lines can be attributed to dopant material near the illuminated surface of the device. Relatively small values of $k(\lambda)$ indicate that light of that particular wavelength can penetrate far into the sample to provide information about the concentration of the dopant material in deeper regions of the sample.

Typically, the wavelengths chosen for obtaining the Raman spectra should reflect a range of $k(\lambda)$ values. Preferably, at least one of the wavelengths of light has a k(l) value which is no less than one half the value of the estimated limit of substantial dopant penetration. The other wavelengths of light are chosen so that there is a range of $k(\lambda)$ values which spans the expected depth of the dopant.

In another embodiment, the wavelengths of light are chosen based upon the availability and convenience of light sources. For example, the wavelengths may be chosen because some or all of the wavelengths are available from a single laser source. Visible, near infrared, and ultraviolet light may be used to determine the depth profile and/or depth profile characteristics.

Returning to FIG. 8, block 802 represents the determination of the intensity characteristics of the appropriate Raman lines (i.e., the Raman lines attributable to the dopant materials) for the target region of the semiconductor device. This typically includes illuminating the target region of the two or more illumination wavelengths and measuring the intensity characteristics of the appropriate Raman line(s).

After determining the profile constants and the intensity characteristics of the appropriate Raman lines of the target region, the depth profile of the target region is determined, as indicated at Block 804. The depth profile may, for example, be determined from the intensity relationship in equations (3) or (4) using the profile constants and the appropriate intensity characteristics as data.

In another embodiment, one or more of the depth profile parameters are determined by other methods, such as estimations of the position of the peak concentration or the concentration of the dopant from the implant parameters. The depth profile or other depth profile parameters may then be determined, according to the flow illustrated in FIG. 8.

In yet another embodiment, it may be sufficient to determine one or more of the depth profile characteristics or at least establish that the characteristic(s) is within a range or above or below a threshold value. This may be accomplished using measurements at one or more illumination wavelengths. For example, the width characteristic of a dopant distribution may be determined by a single measurement using a single illumination wavelength and estimates of the peak position and concentration of the dopant.

Turning back to FIG. 2, one exemplary system for determining the depth profile and/or depth profile characteristics of a dopant material in a semiconductor device will be described. Consistent with this embodiment, a semiconductor device 14 is conveyed to a depth profiler 10 which includes a Raman spectroscopic apparatus. The semiconductor device 14 is illuminated with light 18 having an illumination wavelength. A detector 20 measures an intensity characteristic of scattered light 22 at a particular wavelength or over a wavelength range which corresponds to a spectral line that is attributable to the presence of the dopant material in the semiconductor device.

This process is repeated for one or more different illumination wavelengths. The intensity measurements are then provided to a processor (not shown) which uses the intensity measurements directly or calculates other intensity characteristics, such as the integrated intensity over a Raman line. Using previously-determined profile constants (e.g., $A(\lambda)$, $B(\lambda)$, $B(\lambda')$, $k(\lambda)$ and $k(\lambda')$), in concert with the measured or calculated intensity characteristics, the processor determines the depth profile, one or more depth profile characteristics, and/or the concentration of the dopant material in the region of interest of the semiconductor device.

Figure 5:
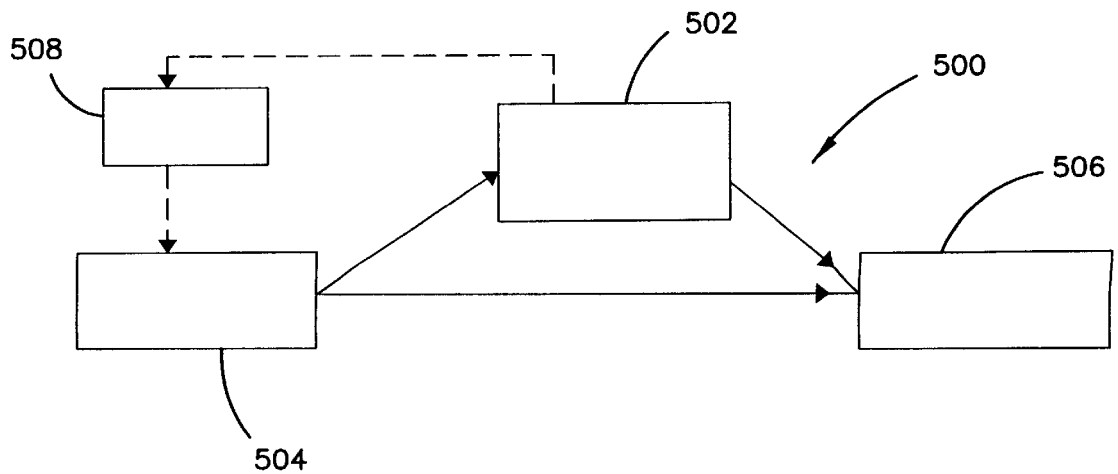
FIG. 5 is a diagrammatic illustration of an exemplary depth profiling apparatus in a fabrication line according to another embodiment of the invention.

Turning now to FIG. 5, there is illustrated an exemplary semiconductor fabrication line 500 incorporating a depth profiling apparatus 502 using a Raman spectroscopic apparatus. It will be understood that a similar fabrication line can be used for determining the depth profile or depth profile characteristics of a dopant material in any layer of a semiconductor device.

The depth profiling apparatus 502 is positioned in the fabrication line 500 downstream from a doping apparatus 504. The doping apparatus 504 dopes a region of the semiconductor device with a dopant material. This may be done, for example, using well-known techniques such as diffusional doping or ion implantation. Optionally, the semiconductor device is annealed to drive the dopant material further into the doped region and/or to provide a more uniformly doped region. A particular set of parameters, for example, temperature, dopant concentration, dopant velocity, and annealing temperature, typically determine, at least in part, the dopant depth profile, one or more depth profile characteristics, and/or concentration of the dopant.

Once a semiconductor device has been doped, the device continues along the fabrication line 500. At least one of the doped semiconductor devices is chosen periodically to be tested using the depth profiling apparatus 502. Other semiconductor devices may continue on to other processing systems 506. The semiconductor devices for testing can be chosen randomly or may be chosen at regular intervals (e.g., every fifth device) or every device may be tested.

The semiconductor device to be tested is conveyed to the depth profiling apparatus 502 and a depth profile or one or more depth profile characteristics of the semiconductor device are determined, for example, by the methods described above. The depth profile or the one or more depth profile characteristics may be recorded for quality control purposes. An optional alarm may be provided which alerts a user or device when the depth profile or the one or more depth profile characteristics of a tested semiconductor device deviate beyond a threshold value or values.

In some embodiments, the determined depth profile or the one or more depth profile characteristics are provided to a processor 508 which compares the determined depth profile or the one or more depth profile characteristics to the desired depth profile or depth profile characteristics and if the determined depth profile or depth profile characteristics deviates by a threshold amount, then the processor 508 provides instructions to the doping apparatus 504 to alter the doping parameters. This provides a feedback loop for the maintenance of the proper depth profile of dopant material.

Typically, the determination of the depth profile or depth profile characteristics by Raman spectroscopy only takes seconds or minutes. This allows the fabrication line 500 to respond quickly to deviations from a desired dopant depth profile. This provides for a continuous updating of the dopant parameters for changing conditions and also provides a method of determining when equipment is failing without producing an excessive number of inadequate or faulty devices. Furthermore, because the depth profile determination method using Raman spectroscopy is entirely non-invasive, the tested semiconductor devices can be returned to the processing line 500 and the later processing devices 506.

The present invention should not be considered limited to the particular examples described above, but rather should be understood to cover all aspects of the invention as fairly set out in the attached claims. Various modifications, equivalent processes, as well as numerous structures to which the present invention may be applicable will be readily apparent to those of skill in the art to which the present invention is directed upon review of the present specification. The claims are intended to cover such modifications and devices.

We claim:

1. A method for determining at least one depth profile characteristic of a dopant material in a region of a semiconductor device, comprising:
    illuminating the region with light at each of two or more illumination wavelengths to produce scattered light;
    integrating the intensity of the scattered light over at least a portion of at least one spectral line and determining, for each one of the two or more illumination wavelengths, an intensity characteristic of the scattered light for the spectral line, at a wavelength different than the one of the two or more illumination wavelengths, which is attributable to the dopant material; and
    determining the at least one depth profile characteristic of the dopant material using each intensity characteristic and illumination wavelength.

2. The method of claim 1, wherein the at least one depth profile characteristic is a position of a peak concentration of the dopant material, a width characteristic of a distribution of the dopant material, or combinations thereof.

3. The method of claim 1, further comprising determining a depth profile of the dopant material using the determined at least one depth profile characteristic and a determined concentration of the dopant material.

4. The method of claim 1, wherein the region is illuminated by light from a laser.

5. The method of claim 1, wherein the region is illuminated by visible light.

6. The method of claim 1, wherein the semiconductor device comprises silicon.

7. The method of claim 1, wherein the dopant material comprises boron, arsenic, phosphorus, or nitrogen.

8. The method of claim 1, wherein the semiconductor device comprises a substrate and the region of the semiconductor device which contains the dopant comprises a portion of the substrate.

9. The method of claim 1, wherein the semiconductor device comprises a substrate and the region of the semiconductor device which contains the dopant comprises a doped layer formed over at least a portion of the substrate.

10. The method of claim 1, wherein each of the one or more spectral lines comprises a Raman spectral line.

11. A method for determining a depth profile of a dopant material in a region of a semiconductor device, comprising:
    illuminating the region with light at each of two or more illumination wavelengths to produce scattered light;
    determining, for each one of the two or more illumination wavelengths, an intensity characteristic of the scattered light for at least one spectral line, at a different wavelength than the one of the two or more illumination wavelengths, which is attributable to the dopant material;
    obtaining, for each illumination wavelength, an absorption coefficient of light from a test semiconductor device which is similar to the semiconductor device; and
    determining the depth profile of the dopant material using each intensity characteristic, absorption coefficient, and illumination wavelength.

12. The method of claim 11, wherein each absorption coefficient is obtained for a similar semiconductor device with a same dopant material as the semiconductor device.

13. The method of claim 11, wherein each absorption coefficient is determined by ellipsometry.

14. A method for determining a depth profile of a dopant material in a region of a semiconductor device comprising:

illuminating the region with light at each of two or more illumination wavelengths to produce scattered light;

determining, for each one of the two or more illumination wavelengths, an intensity characteristic of the scattered light for at least one spectral line, at a different wavelength than the one of the two or more illumination wavelengths, which is attributable to the dopant material, wherein the relationship between each intensity characteristic and the corresponding wavelength is defined by:

$$I = A(\lambda, \lambda')B(\lambda)B(\lambda') \int_0^T e^{\frac{-4\pi k(\lambda)z}{\lambda}} C(z) e^{\frac{-4\pi k(\lambda')z}{\lambda'}} dz$$

where I is a particular one of the intensity characteristics, $\lambda$ is the particular illumination wavelength corresponding to the particular intensity characteristic, $\lambda'$ is a wavelength of the spectral line which is attributable to the dopant material, $A(\lambda,\lambda')$, $B(\lambda)$, and $B(\lambda')$ are profile constants dependent upon the particular illumination and spectral line wavelengths, T is the thickness of the region of the semiconductor device, $k(\lambda)$ is the absorption coefficient of the region of the particular illumination wavelength, $k(\lambda')$ is the absorption coefficient of the spectral line wavelength, z is the depth of the region, and $C(z)$ is the depth profile;

obtaining, for each illumination wavelength, an absorption coefficient of light from a test semiconductor device which is similar to the semiconductor device; and determining the depth profile of the dopant material using each intensity characteristic, absorption coefficient, and illumination wavelength.

15. A method for determining a depth profile of a dopant material in a region of a semiconductor device, the method comprising:

illuminating the region with light at two or more illumination wavelengths;

obtaining for each one of the two or more illumination wavelengths at least a portion of at least one associated Raman spectrum;

integrating the intensity of each Raman spectrum over at least a portion of one or more spectral lines and determining, for each Raman spectrum, an intensity characteristic of the one or more spectral lines, at a wavelength different than the one of the two or more illumination wavelengths, attributable to the dopant material; and using each intensity characteristic and the respective illumination wavelength to determine the depth profile of the dopant material in the region.

16. A method for in-line determination of at least one depth profile characteristic for a plurality of semiconductor devices, comprising:

doping a target region of each of the semiconductor devices with a dopant material using a set of dopant parameters;

choosing at least one test semiconductor device from the semiconductor devices;

illuminating the target region of the test semiconductor device with light at at least two illumination wavelengths to produce scattered light;

integrating the intensity of the scattered light over at least a portion of one or more spectral lines and determining, for each one of the at least two illumination wavelengths, an intensity characteristic of the scattered light for the one or more spectral lines, at a wavelength different than the one of the at least two illumination wavelengths, attributable to the dopant material; and determining the at least one depth profile characteristic of the dopant material using the intensity characteristic and the at least two illumination wavelengths.

17. The method of claim 16, wherein the at least one depth profile characteristic is a position of a peak concentration of the dopant material, a width characteristic of a concentration distribution of the dopant material, or a combination thereof.

18. The method of claim 16, wherein the method further comprises altering the dopant parameters based on the depth profile of the test semiconductor device to achieve a desired depth profile in subsequently-manufactured one of the semiconductor devices.

19. An apparatus for the production of semiconductor devices, the apparatus comprising:

a doping apparatus for doping a region of the semiconductor devices with a dopant material; and an in-line apparatus comprising a light source capable of producing light at two or more illumination wavelengths, a detector to measure an intensity of light scattered from a semiconductor device which is illuminated by the light source, the detector measuring, at each one of the two or more illumination wavelengths, the intensity of light for one or more spectral lines having a wavelength different than the one of the two or more illumination wavelengths, and a processor configured to integrate the intensity of the scattered light over at least a portion of each of the one or more spectral lines to determine the depth profile.

20. The apparatus of claim 19, wherein the in-line apparatus provides signals to the doping apparatus to adjust a set of doping parameters based on the at least one determined depth profile characteristic of the one or more doped semiconductor devices.

21. The apparatus of claim 19, wherein the in-line apparatus is a Raman spectrometer.

22. An apparatus for determining the depth profile of a dopant material in a semiconductor device, the apparatus comprising:

a light source capable of producing light at two or more illumination wavelengths;

a detector to measure an intensity of light scattered from a semiconductor device which is illuminated by the light source, the detector measuring, at each one of the two or more illumination wavelengths, the intensity of light for one or more spectral lines having a wavelength different than the one of the two or more illumination wavelengths; and a processor configured to integrate the intensity of the scattered light over at least a portion of each of the one or more spectral lines to determine the depth profile from the measured intensities.

* * * * *